United States Patent [19]
van der Maas

[11] Patent Number: 5,837,038
[45] Date of Patent: Nov. 17, 1998

[54] CLOSING ELEMENT INTENDED FOR CLOSING OFF AN END OF A CAPILLARY GAS CHROMATOGRAPHY COLUMN

[75] Inventor: Martinus Frans van der Maas, Arnemuiden, Netherlands

[73] Assignee: SGT Exploitatie B.V., Netherlands

[21] Appl. No.: 887,976

[22] Filed: Jul. 3, 1997

[30] Foreign Application Priority Data

Jul. 5, 1996 [NL] Netherlands ............ 1003526

[51] Int. Cl.$^6$ .................................................. B01D 15/08
[52] U.S. Cl. ............................................................. 96/101
[58] Field of Search ................ 96/101–107; 73/23.39; 210/198.2

[56] References Cited

U.S. PATENT DOCUMENTS

| | | | |
|---|---|---|---|
| 4,389,313 | 6/1983 | Charney et al. | 96/104 X |
| 4,393,882 | 7/1983 | White | 128/764 |
| 4,394,263 | 7/1983 | Dosch et al. | 96/104 X |
| 4,422,860 | 12/1983 | Feinstein | 96/105 X |
| 4,440,550 | 4/1984 | Jenkins et al. | 96/105 X |
| 4,476,016 | 10/1984 | Kiyasu | 210/198.2 |
| 4,737,292 | 4/1988 | Ritacco et al. | 96/101 X |
| 4,787,656 | 11/1988 | Ryder | 96/106 X |
| 4,956,298 | 9/1990 | Diekmann | 430/311 |
| 4,969,938 | 11/1990 | America | 96/105 |
| 5,395,521 | 3/1995 | Jagadeeswaran | 96/103 X |
| 5,540,464 | 7/1996 | Picha | 96/106 X |

FOREIGN PATENT DOCUMENTS

| | | |
|---|---|---|
| 0 636 882 A1 | 2/1995 | European Pat. Off. . |
| 0 706 047 A | 4/1996 | European Pat. Off. . |
| 0134463 | 12/1979 | Germany ............ 96/101 |
| 4114914 | 11/1992 | Germany ............ 96/101 |
| 62-231167 A | 10/1987 | Japan . |
| WO89/07759 | 8/1989 | WIPO ............ 96/101 |

OTHER PUBLICATIONS

Dutch Novelty Search Report for Priority Application No. NL 1003526 dated Jul. 5, 1996.

*Primary Examiner*—Robert Spitzer
*Attorney, Agent, or Firm*—Dehlinger & Associates

[57] ABSTRACT

A closing element intended for closing off an end of a capillary gas chromatography column comprises a closing body provided with a blind hole, which tapers over at least a portion of the length thereof, and the walls of the tapering portion of the hole include an angle with the centerline of the hole, this angle being so small that upon placement of the closing element on the end of the capillary gas chromatography column, a self-locking engagement between the end of the column and the closing element occurs. The closing element is manufactured from a form-retaining, inert, gastight material.

5 Claims, 1 Drawing Sheet

CLOSING ELEMENT INTENDED FOR CLOSING OFF AN END OF A CAPILLARY GAS CHROMATOGRAPHY COLUMN

This application claims the priority of Dutch Patent Application No. 1003526 filed Jul. 5, 1996, which is incorporated herein by reference.

1. Field of the Invention

The present invention relates to a closing element intended for closing off an end of a capillary gas chromatography column with a certain external column diameter.

2. Background of the Invention

The capillary gas chromatography columns known per se are provided on the inside with a coating which furnishes the gas chromatographic action to the column. On the outside the known columns are typically provided with a polyamide coating which inter alia improves the breaking strength of the column. The internal coating is affected by oxygen, so that the column should be closed off after being manufactured and when it is not being used for some time.

Some manufacturers close off the column after the production thereof by melting up the ends. When putting such a column into use, the melted-up ends must be carefully removed without thereby damaging the intrinsically fragile capillary column. Putting a thus designed capillary gas chromatography column into use is therefor risky and requires reasonable skill. Once the column has been used, it should be closed off after use in order to prevent damage to the internal coating by oxygen. This closure occurs in practice with a so-called septum. Some manufacturers use such septa also for closing off the newly produced gas chromatography columns instead of melting them up.

In the subject field of the art, a septum is understood to mean a rubber disc with a side of a thickness of about 2 mm and a diameter of about 10 mm. In practice, the needle-shaped end of the column is inserted in the side of the septum. A drawback of thus closing off the column is that the danger exists that rubber is left behind in the capillary of the column. The rubber left behind can cause a considerable disturbance of the gas chromatography measurement. Another drawback of the septum manufactured from rubber is that it is yet possible for substances to diffuse through or from the septum to the coating, which substances can likewise disturb the measurements.

SUMMARY OF THE INVENTION

The object of the invention is to provide a closing element for capillary gas chromatography columns without the above-indicated drawbacks.

In one aspect, the invention includes, a closing element intended for closing off an end of a capillary gas chromatography column with a certain external column diameter (Dk). The closing element comprises a closing body provided with a blind hole which tapers over at least a portion of the length thereof, when viewed from the opening of the blind hole towards the blind end of the hole. The tapering portion of the blind hole has at its end proximal to the opening a diameter (Db) greater than the external column diameter (Dk). The diameter (De) of the tapering portion of the blind hole at the end thereof remote from the opening is smaller than the external diameter of the column (Dk). The walls of the tapering portion of the blind hole include an angle with the centerline of the hole which is so small that upon placement of the closing element on the end of the capillary gas chromatography column a self-locking engagement between the end of the column and the closing element occurs. The closing element is manufactured from a form-retaining, inert, gastight material.

In one embodiment, the closing element is characterized in that the form-retaining, inert, gastight material is glass. In another embodiment, the form-retaining, inert, gastight material is ceramic. In another embodiment, the form-retaining, inert, gastight material is metal, such as stainless steel, copper, silver, gold, or a metal alloy with similar inert properties.

The closing element, in another embodiment, is characterized in that at the end of the blind hole proximal to the opening, a funnel-shaped hole portion is provided. A funnel mouth defines the opening of the hole, while the end of the funnel-shaped hole portion remote from the funnel mouth has a diameter (Dt) corresponding to the diameter (Db) of the tapering portion of the blind hole at the end thereof proximal to the opening, and the diameter (Do) of the opening is considerably greater than the external diameter (Dk) of the capillary column, so that placement of the closing element on the end of the column is simple.

DETAILED DESCRIPTION OF THE INVENTION

Figure 1:
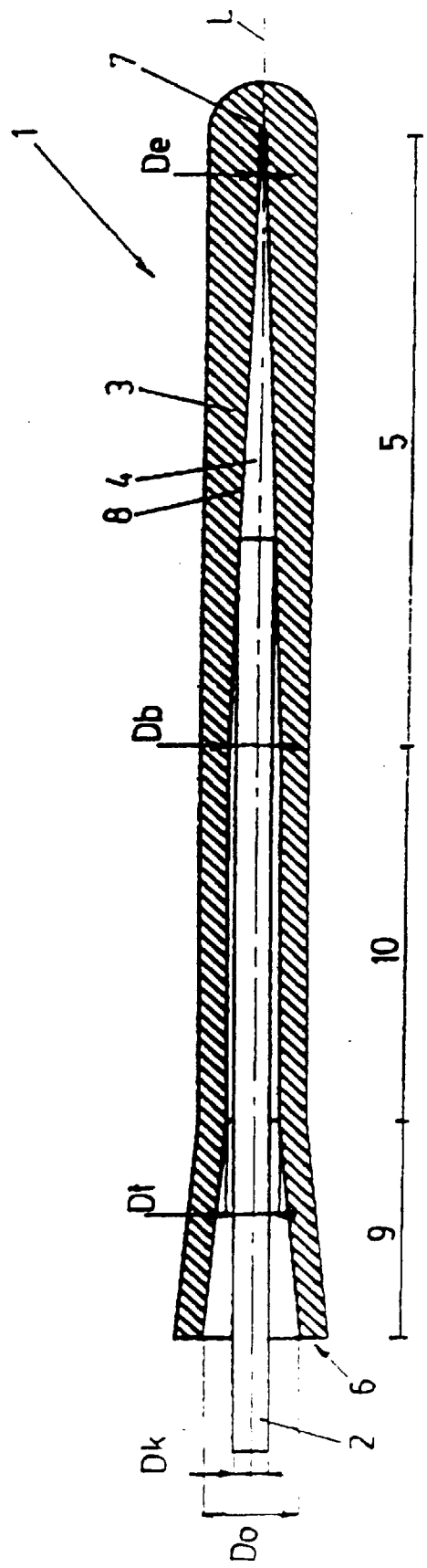
FIG. 1 is a schematic illustration of the closing element in accordance with the present invention.

The closing element according to the invention comprises a closing body provided with a blind hole, the hole tapering over at least a portion of the length thereof, viewed from the opening to the blind end of the hole, the tapering portion of the hole having at its end proximal to the opening a diameter greater than the external column diameter, while the diameter of the tapering portion of the hole at its end remote from the opening is smaller than the external diameter of the column, the walls of the tapering portion of the hole including an angle with the centerline of the hole, which is so small that upon placement of the closing element on the end of the capillary gas chromatography column a self-locking engagement between the end of the column and the closing element occurs, the closing element being made of a form-retaining, inert, gastight material.

Owing to the self-locking angle of the tapering hole portion, a closing element of such design made from form-retaining, inert, gastight material automatically remains fixed on the end of the capillary column. Moreover, a hermetic sealing of the end of the capillary column is obtained, through which no gases can diffuse. The closing element according to the invention is easy to fit and remove, so that any chance of breakage of the capillary column is minimized. Further, upon removal of the closing element, no parts thereof are left behind on the column, so that disturbance of the gas chromatogram is prevented.

According to a further elaboration of the invention, the form-retaining, inert, gastight material is glass. A closing element made of glass is cheap and moreover provides the advantage of being transparent. When the closing element is properly placed on the end of a capillary column, an annular contact surface becomes visible, which affords the user a possibility of checking whether a good closure has been obtained.

Other possible materials for the manufacture of the closing element are ceramic or metal, such as stainless steel, copper, silver, gold, or a metal alloy having similar inert properties. In connection with the price, however, glass is preferred.

In order to facilitate placing the closing element on the end of a gas chromatography column, the closing element is characterized, according to a further elaboration of the invention, in that at the end of the hole proximal to the opening, a funnel-shaped hole portion is provided, of which a funnel mouth defines the opening of the hole, while the end of the funnel-shaped hole portion remote from the funnel mouth has a diameter corresponding to the diameter of the tapering hole portion at its end proximal to the opening, and the diameter of the opening is considerably greater than the external diameter of the capillary column.

The invention will be further clarified on the basis of an exemplary embodiment represented in the accompanying drawing.

The exemplary embodiment of the closing element 1 represented in the drawing is represented at 10 magnifications. The external diameter Dk of the end of the capillary gas chromatography column shown is about 0.5 mm. The length of the closing element 1 shown is about 20 mm in reality. The closing element 1 comprises a closing body 3 which is provided with a blind hole 4. The blind hole tapers over at least a portion 5 of the length thereof, viewed from the opening 6 towards the blind end 7 of the hole. The tapering portion 5 of the hole 4 has at its end proximal to the opening 6 a diameter Db greater than the external column diameter Dk. At the end 7 of the tapering portion 5 remote from the opening 6, the diameter is less than the external diameter of the column Dk. The walls 8 of the tapering portion 5 of the hole 4 include an angle with the centerline L of the hole 4 which is so small that upon placement of the closing element 1 on the end of the capillary gas chromatography column 2, a self-locking engagement between the end of the column 2 and the closing element 1 occurs. Clearly, the magnitude of this angle is dependent on the coefficient of friction of the materials of the column 2 and the closing element 1 which are in mutual engagement. In the present exemplary embodiment, this angle is about 1.75°. It will be clear, however, that this angle can vary considerably depending on the coefficient of friction and will be in the range of about 0.1° to about 10°.

The closing element 1 is made from a form-retaining, inert, gastight material. In the present exemplary embodiment, for reasons of cost, glass has been chosen for this material, glass having the additional advantage of being transparent, so that it can be simply checked if the closing element 1 has been fitted properly. As already noted hereinabove, other materials can also be suitable for the manufacture of the closing element 1, such, for instance, ceramic or metal. At the end of the hole 4 proximal to the opening 6, the hole 4 is provided with a funnel-shaped hole portion 9. The funnel mouth defines the opening 6 of the hole 4. The end of the funnel-shaped hole portion 9 remote from the funnel mouth 6 has a diameter Dt corresponding to the diameter Db of the tapering portion 5 of the hole 4 at its end proximal to the opening 6. The diameter Do of the opening 6 is considerably greater than the external diameter Dk of the capillary column 2, so that placement of the closing element 1 on the end of the column 2 is simple. In the present exemplary embodiment, the hole 4 further comprises, between the tapering portion 5 and the funnel-shaped portion 9, a cylindrical portion 10 which serves to increase the maneuverability of the closing element somewhat and to minimize the possibility of the closing element 1 skewing with respect to the column 2.

It will be clear that the invention is not limited to the exemplary embodiment described, but that various modifications are possible within the scope of the invention.

It is claimed:

1. A closing element intended for closing off an end of a capillary gas chromatography column (2) with a certain external column diameter (Dk), the closing element (1) comprising a closing body (3) provided with a blind hole (4), the blind hole (4) tapering over at least a portion (5) of the length thereof, viewed from an opening (6) towards a blind end (7) of the hole (4), the tapering portion (5) of the hole (4) having at its end proximal to the opening (6) a diameter (Db) greater than the external column diameter (Dk), while a diameter (De) of the tapering portion (5) of the hole (4) at the end (7) thereof remote from the opening (6) is smaller than the external diameter of the column (Dk), the walls (8) of the tapering portion (5) of the hole (4) including an angle with the centerline (L) of the hole (4) which is so small that upon placement of the closing element (1) on the end of the capillary gas chromatography column (2) a self-locking engagement between the end of the column (2) and the closing element (1) occurs, the closing element (1) being manufactured from a form-retaining, inert, gastight material.

2. A closing element according to claim 1, characterized in that the form-retaining, inert, gastight material is glass.

3. A closing element according to claim 1, characterized in that the form-retaining, inert, gastight material is ceramic.

4. A closing element according to claim 1, characterized in that the form-retaining, inert, gastight material is a metal selected from the group consisting of stainless steel, copper, silver, gold, and a metal alloy with similar inert properties.

5. A closing element according to claim 1, characterized in that at the end of the hole (4) proximal to the opening (6) a funnel-shaped hole portion (9) is provided, of which a funnel mouth defines the opening (6) of the hole (4), while the end of the funnel-shaped hole portion (9) remote from the funnel mouth (6) has a diameter (Dt) corresponding to the diameter (Db) of the tapering portion (5) of the hole (4) at the end thereof proximal to the opening (6), and a diameter (Do) of the opening (6) is considerably greater than the external diameter (Dk) of the capillary column (2), so that placement of the closing element (1) on the end of the column is simple.

* * * * *